(12) United States Patent
Ito et al.

(10) Patent No.: US 7,892,219 B2
(45) Date of Patent: Feb. 22, 2011

(54) DISPOSABLE WEARING ARTICLE PROVIDED WITH TAPE FASTENERS

(75) Inventors: Kyoko Ito, Kagawa-ken (JP); Kyota Saito, Kagawa-ken (JP)

(73) Assignee: Uni-Charm Co., Ltd., Ehime (JP)

( * ) Notice: Subject to any disclaimer, the term of this patent is extended or adjusted under 35 U.S.C. 154(b) by 870 days.

(21) Appl. No.: 10/833,337

(22) Filed: Apr. 28, 2004

(65) Prior Publication Data

US 2004/0267227 A1    Dec. 30, 2004

Related U.S. Application Data

(63) Continuation of application No. PCT/JP02/13195, filed on Dec. 17, 2002.

(30) Foreign Application Priority Data

Dec. 17, 2001  (JP) ............... 2001-383685
Feb. 1, 2002   (JP) ............... 2002-026017

(51) Int. Cl.
  *A61F 13/60*   (2006.01)
  *A61F 13/551*  (2006.01)
(52) U.S. Cl. ............... 604/385.31; 604/390
(58) Field of Classification Search ............ 604/386, 604/389–391, 385.31
  See application file for complete search history.

(56) References Cited

U.S. PATENT DOCUMENTS

| 3,783,871 A | 1/1974 | Sabee |
| 3,874,386 A | 4/1975 | Kozak |
| 4,177,812 A | 12/1979 | Brown et al. |
| 4,237,890 A | 12/1980 | Laplanche |
| 4,317,449 A | 3/1982 | Nowakoski |
| 4,670,012 A * | 6/1987 | Johnson ............... 604/390 |
| 5,182,156 A | 1/1993 | Pape et al. |

(Continued)

FOREIGN PATENT DOCUMENTS

EP    623330 A2 *   11/1994

(Continued)

OTHER PUBLICATIONS

Translations of JP10-85254-A and 13-046436.*

(Continued)

*Primary Examiner*—Karin M Reichle
(74) *Attorney, Agent, or Firm*—Lowe, Hauptman, Ham & Berner, LLP

(57) ABSTRACT

A disposable wearing article has a first surface and a second surface. The second surface is provided with a tape fastener attached thereto. The tape fastener may be folded so as to be unfoldable in a longitudinal direction and includes a first tape strip and a second tape strip underlying the first tape strip. The first tape strip has a free end zone and a first end zone and is adhesively attached to the second tape strip. The second tape strip has a fixed end zone secured to the second surface and a second end zone. The first end zone of the first tape strip has an extension that extends beyond the second end zone of the second tape strip and is adhesively attached to the second surface either directly or via a third tape strip of the tape fastener.

23 Claims, 9 Drawing Sheets

U.S. PATENT DOCUMENTS

| | | | |
|---|---|---|---|
| 5,279,604 A | 1/1994 | Robertson et al. | |
| 5,591,521 A | 1/1997 | Arakawa et al. | |
| 6,063,065 A | 5/2000 | Costa | |
| 6,264,644 B1 * | 7/2001 | Igaue et al. | 604/389 |
| 6,328,725 B2 | 12/2001 | Fernfors | |
| 6,371,949 B1 * | 4/2002 | Soga et al. | 604/385.13 |
| 6,475,205 B2 | 11/2002 | Shimada et al. | |
| 6,638,261 B2 | 10/2003 | Suzuki | |
| 6,926,704 B2 | 8/2005 | Andersson et al. | |
| 2001/0011168 A1 | 8/2001 | Shimada et al. | |
| 2002/0026172 A1 | 2/2002 | Shimada et al. | |
| 2002/0052593 A1 | 5/2002 | Kurita et al. | |
| 2003/0014030 A1 * | 1/2003 | Andersson et al. | 604/385.13 |
| 2005/0070868 A1 | 3/2005 | Ito et al. | |
| 2006/0206092 A1 | 9/2006 | Shimoe | |

FOREIGN PATENT DOCUMENTS

| | | |
|---|---|---|
| EP | 0 815 820 A2 | 1/1998 |
| GB | 1 441 567 | 7/1976 |
| JP | 50-109041 A | 8/1975 |
| JP | 5-39531 | 5/1993 |
| JP | 06-077719 U | 11/1994 |
| JP | 9-253125 | 9/1997 |
| JP | 10/085254 | 4/1998 |
| JP | 10-211231 A | 8/1998 |
| JP | 2000-502573 | 3/2000 |
| JP | 2001-46436 A | 2/2001 |
| JP | 2001-178777 A | 7/2001 |
| KR | 8-507699 | 8/1996 |
| WO | 94/09736 | 5/1994 |
| WO | WO 0113842 A1 * | 3/2001 |
| WO | 2003/022195 | 3/2003 |

OTHER PUBLICATIONS

Dictionary definitions of "eve" and "attach", Merriam-Webster Online.*

* cited by examiner

DISPOSABLE WEARING ARTICLE PROVIDED WITH TAPE FASTENERS

This application is a continuation of International Application No. PCT/JP02/13195 filed Dec. 17, 2002, which claims priority to Japanese Application Nos. 2001-383685 and 2002-26017 filed Dec. 17, 2001 and Feb. 1, 2002, respectively, all of which are hereby incorporated by reference herein in their entirety.

BACKGROUND OF THE INVENTION

This invention relates to a disposable wearing article provided with tape fasteners.

FIG. 9 of the accompanying drawings is a side view showing an adhesive tape fastener 102 disclosed in U.S. Pat. No. 4,177,812. This tape fastener 102 is used, for example, to connect front and rear waist regions to each other to wear an open-type disposable diaper. The tape fastener 102 illustrated therein comprises a tape strip 111, an adhesive 112 applied on a lower surface 111d of the tape strip 111 and a release paper sheet 113. The tape strip 111 is folded in a Z-shape and attached to the associated one of transversely opposite side edge zones 115a of the diaper. The tape strip 111 folded in this manner defines a top layer 111a, a bottom layer 111b and an intermediate layer 111c and the release paper sheet 113 is secured by the adhesive 112 to the intermediate layer 111c without a possibility that the release paper sheet 113 might be easily peeled off. To prevent the respective layers 111a, 111b and 111c of the tape fastener 102 from being unfolded prior to actual use of the tape fastener 102, the top layer 111a is releasably attached to the release paper sheet 113 with the adhesive 112 so that these top layer 111a may be easily peeled off from the release paper sheet 113. Similarly, the intermediate layer 111c is releasably attached to an adhesive 116 applied on a bottom layer 111b so that the intermediate layer 111c may be easily peeled off from the adhesive 116. For actual use, the tape fastener 102 is pulled leftward with its end zone 120 held by the fingers. The intermediate layer 111c of the tape strip 111 is peeled off from the adhesive 116, then the top layer 111a is peeled off together with the adhesive 112 from the release paper sheet 113 and thus the tape fastener 102 is rectilinearly folded out. Thereafter, the top layer 111a is used to connect the front and rear waist regions to each other.

In the conventional tape fastener 102, a force exerted on the top layer 111a and the intermediate layer 111c in a direction indicated by arrow Q in FIG. 9 causes the intermediate layer 111c to be peeled off the adhesive 116 in a direction indicated by arrow R. It is uneasy to hold the end zone 120 of the tape fastener 102 after the intermediate layer 111c has been peeled off the adhesive 116.

SUMMARY OF THE INVENTION

It is an object of this invention to improve a disposable wearing article provided with folded tape fasteners adapted to be unfolded for actual use of the article so that these tape fasteners are not unintentionally peeled off from the wearing article but easily unfolded when these tape fasteners are actually used.

According to this invention, there is provided a disposable wearing article having a first surface facing a wearer's body and a second surface facing a garment, the article comprising an adhesive tape fastener disposed to the second surface, the tape fastener having a free end zone and a fixed end zone opposed to each other in a longitudinal direction, the fixed end zone being secured to the second surface, the tape fastener being disposed to the wearing article in a folded posture, the tape fastener being unfolded in a direction from the fixed end zone toward the free end zone with the free end zone being held, and the tape fastener having an inner surface facing the second surface in an unfolded state and being partially coated with an adhesive.

The disposable wearing article further comprises a first tape strip having the free end zone and a first end zone opposed to the free end zone in the longitudinal direction; a second tape strip underlying the first tape strip so as to face the second surface and having the fixed end zone and a second end zone opposed to the fixed end zone and being connected to the first end zone of the first tape strip at the second end zone; the first tape strip being coated on the inner surface with the adhesive so as to be releasably attached to the second tape strip underlying the first tape strip, the first end zone including an extension extending from the free end zone toward the first end zone beyond the second end zone of the second tape strip and releasably attached to the second surface; and a region of the second tape strip in which an inner surface of the first tape strip is releasably attached to the second tape strip being not adhesively attached to the second surface opposed to the region so as to be released upwardly from the second surface.

This invention includes the following embodiments.

A third tape strip is interposed between the second tape strip and the second surface and secured over its substantially full length to the second surface and wherein the fixed end zone is adhesively attached to the second surface with the third tape strip therebetween.

The extension of the first tape strip is releasably attached to the second surface with the third tape strip therebetween.

The disposable wearing article is a pants-type disposable diaper having a front waist region, a rear waist region and a crotch region extending between these waist regions, the crotch region is provided with an absorbent core, the front and rear waist regions being connected together along respective transversely opposite side edge portions so as to form a waist-hole and a pair of leg-holes, and the fixed end zone of the second tape strip is adhesively attached to the second surface in each of the side edge portions of at least one of the front or rear waist region so that the longitudinal direction of the second tape strip is parallel to a waist-surrounding direction of the diaper.

The disposable diaper has flaps formed by a sheet material extending outwardly beyond a peripheral edge of the core and the fixed end zone of each said second tape strip is adhesively attached to the second surface in each of the flaps.

A portion of the second surface under each of the tape fastener in a folded posture or a laminated sheet portion including the portion of the second surface and sheet members separately provided in addition to said portion which are overlaid and joined together has a flexural stiffness of $(0.03\text{-}0.7)\times10^{-4}\text{N}\cdot\text{m}^2/\text{m}$.

In the following description of this invention, a flexural stiffness is a value obtained by using the automatic net flexure tester Model KESFB2-AUTO-A of KATO TECH on 100× 100 mm specimen and given in unit of $10^{-4}\text{N}\cdot\text{m}^2/\text{m}$. With the specimen being curved in the direction orthogonal to the direction in which the folded tape fastener will be unfolded, a curvature variation dK from $0.5\text{ cm}^{-1}$ to $1.5\text{ cm}^{-1}$ and a difference dM between bending moments associated with the curvatures of $0.5\text{ cm}^{-1}$ and $1.5\text{ cm}^{-1}$, respectively, are obtained. The ratio dM/dK is the flexural stiffness in this invention. The measuring method of the flexural stiffness in this manner is described in "Textile Engineering", Vol. 33, No. 2.

DETAILED DESCRIPTION OF THE PREFERRED EMBODIMENTS

Details of a disposable wearing article provided with tape fasteners according to this invention will be more fully understood from the description of the disposable diaper as a specific embodiment given hereunder in reference to the accompanying drawings.

Figure 1:
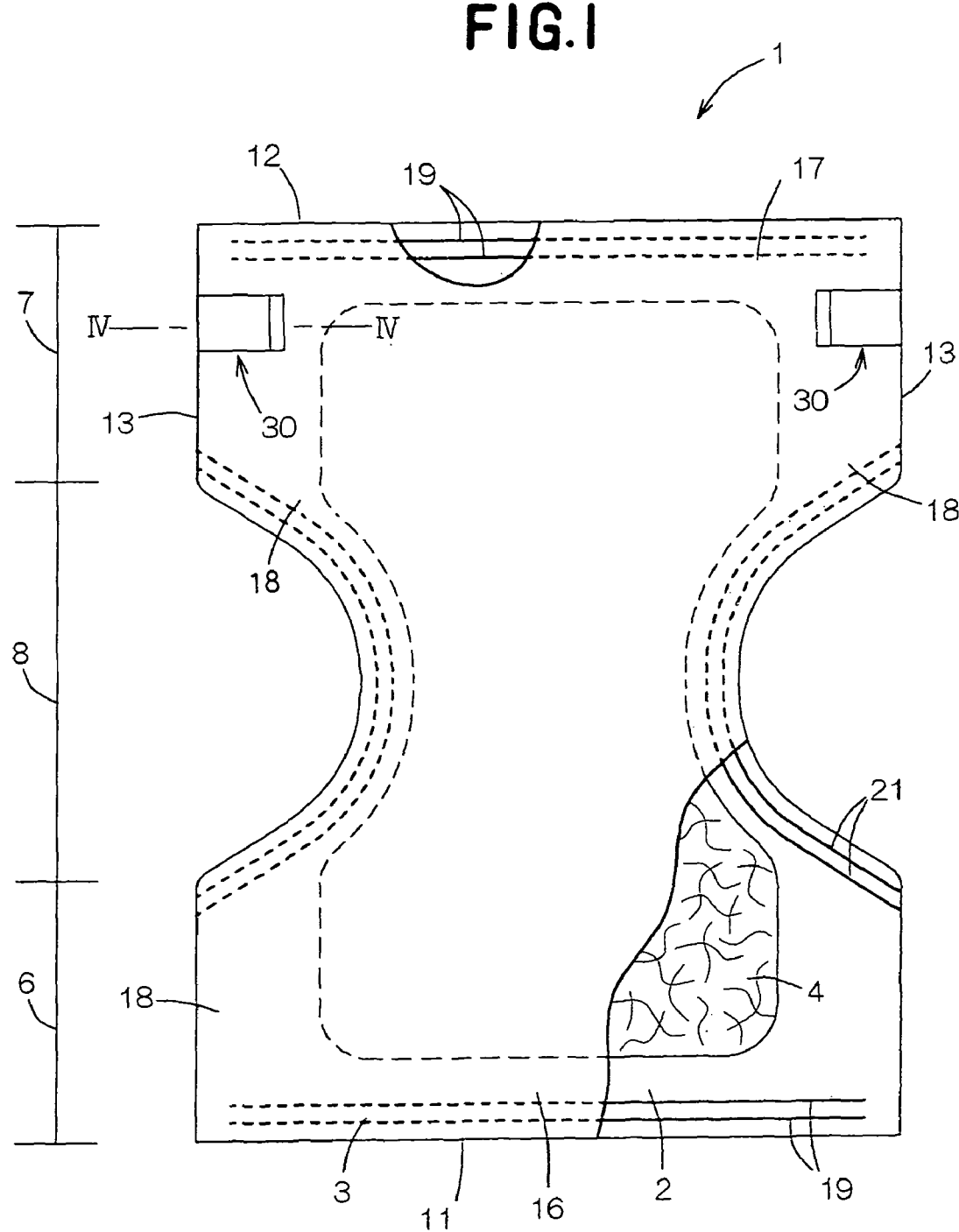
FIG. 1 is a partially cutaway plan view showing the disposable diaper according to this invention.

FIG. 1 is a partially cutaway plan view showing a disposable diaper 1 using tape fasteners 30 according to this invention. The diaper 1 comprises a liquid-pervious topsheet 2 facing a wearer's body, a liquid-impervious backsheet 3 facing a garment and a liquid-absorbent core 4 interposed between these two sheets 2, 3. As viewed in FIG. 1, the backsheet 3 overlies the topsheet 2. The diaper 1 is contoured by a front end 11 and a rear end 12 extending in parallel to each other in a transverse direction and a pair of transversely opposite side edges 13 extending in parallel to each other in a longitudinal direction orthogonal to the transverse direction. The diaper 1 is composed, in the longitudinal direction, of a crotch region 8 defining the middle region, a front waist region 6 being contiguous to the crotch region 8 and extending to the front end 11, and a rear waist region 7 being contiguous to the crotch region 8 and extending to the rear end 12. In the crotch region 8, the side edges 13 curve inwardly. Portions of the top- and backsheets 2, 3 extending outwardly beyond peripheral edge of the core 4 are overlaid and joined together by means of a well-known hot melt adhesive (not shown) to form a front flap 16, a rear flap 17 and a pair of side flaps 18. In the front and rear flaps 16, 17, waist-surrounding elastic members 19 are secured in a stretched state to the inner surface of at least one of the top-and backsheets 2, 3. In the side flaps 18, thigh-surrounding elastic members 21 are stretched along the curved portions of the respective side edges 13 and secured to the inner surface of at least one of the top- and backsheets 2, 3 in a stretched state. In the rear waist region 7, portions of the backsheet 3 defining the side flaps 18 are respectively provided with tape fasteners 30 secured thereto in the vicinity of the side edges 13 and extending in a waist-surrounding direction. These tape fasteners 30 are in folded state and adapted to be unfolded outwardly beyond the side edges 13 of the diaper 1.

Figure 2:
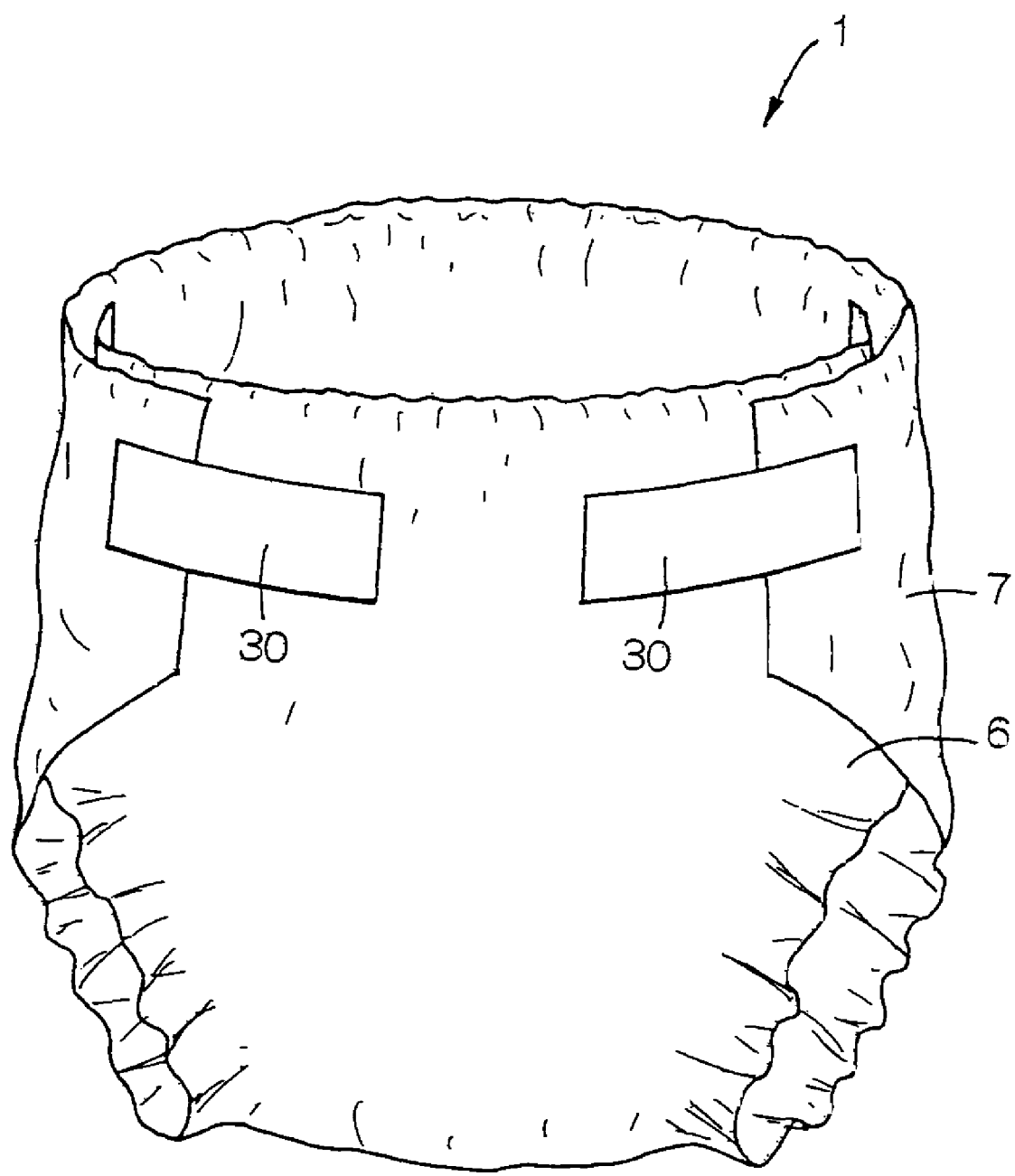
FIG. 2 is a diagram illustrating the manner in which the tape fasteners are used.
Figure 3:
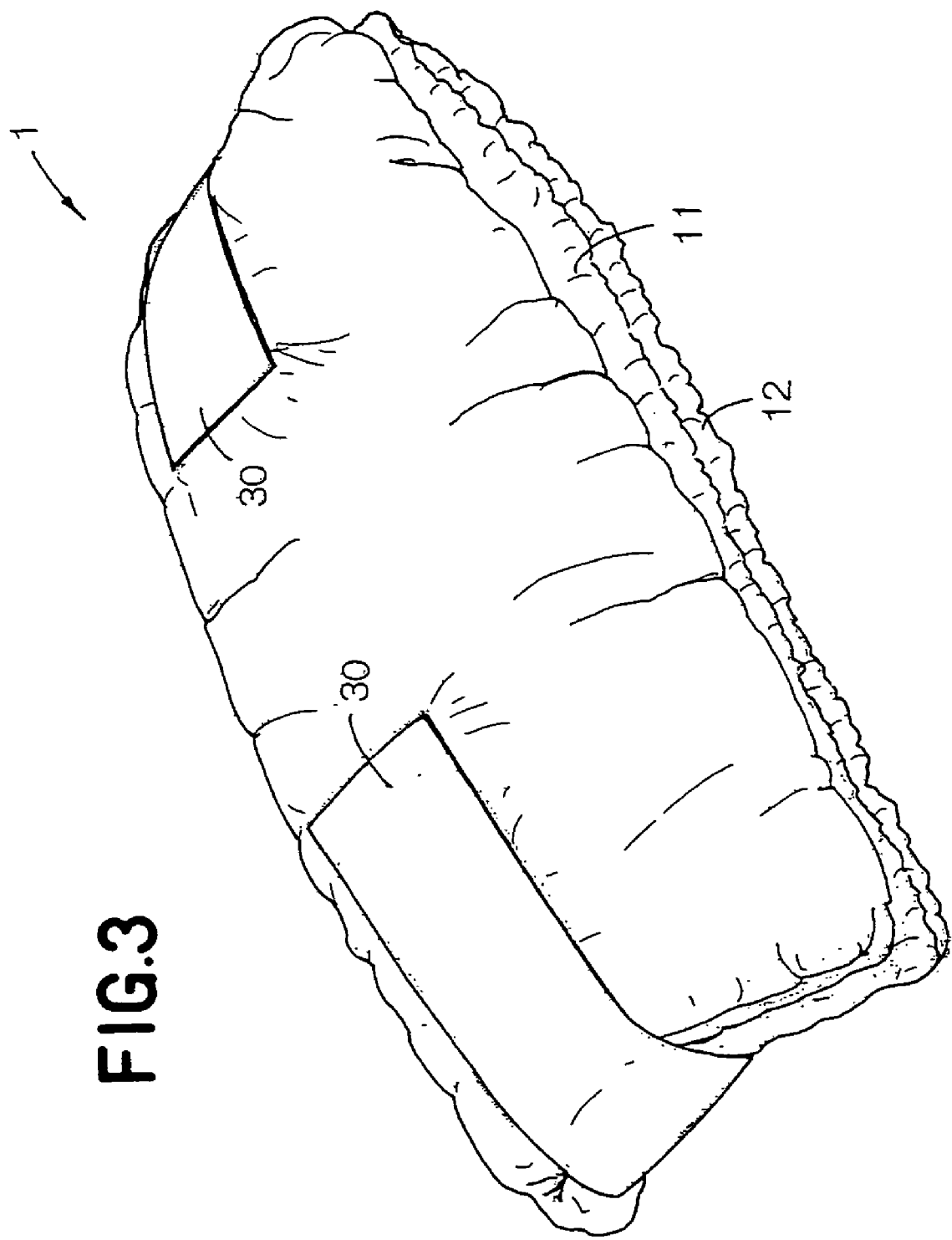
FIG. 3 is a diagram similar to FIG. 2.

FIGS. 2 and 3 are diagrams illustrating the manner in which the tape fasteners 30 are used. FIG. 2 illustrates the diaper 1 as put on the wearer's body with the tape fasteners 30 unfolded so as to extend from the rear waist region 7 and releasably attached to the front waist region 6. FIG. 3 illustrates the used diaper 1 having the front and rear waist regions 6, 7 overlaid each other with the topsheet 2 inside, rolled up together from the crotch region 8 toward the front and rear ends 11, 12 and retained in this rolled up state by the tape fasteners 30. In this manner, the tape fasteners 30 serve as fastening means not only when the diaper 1 is put on the wearer's body but also when the used diaper 1 is rolled up for disposal.

Figure 4:
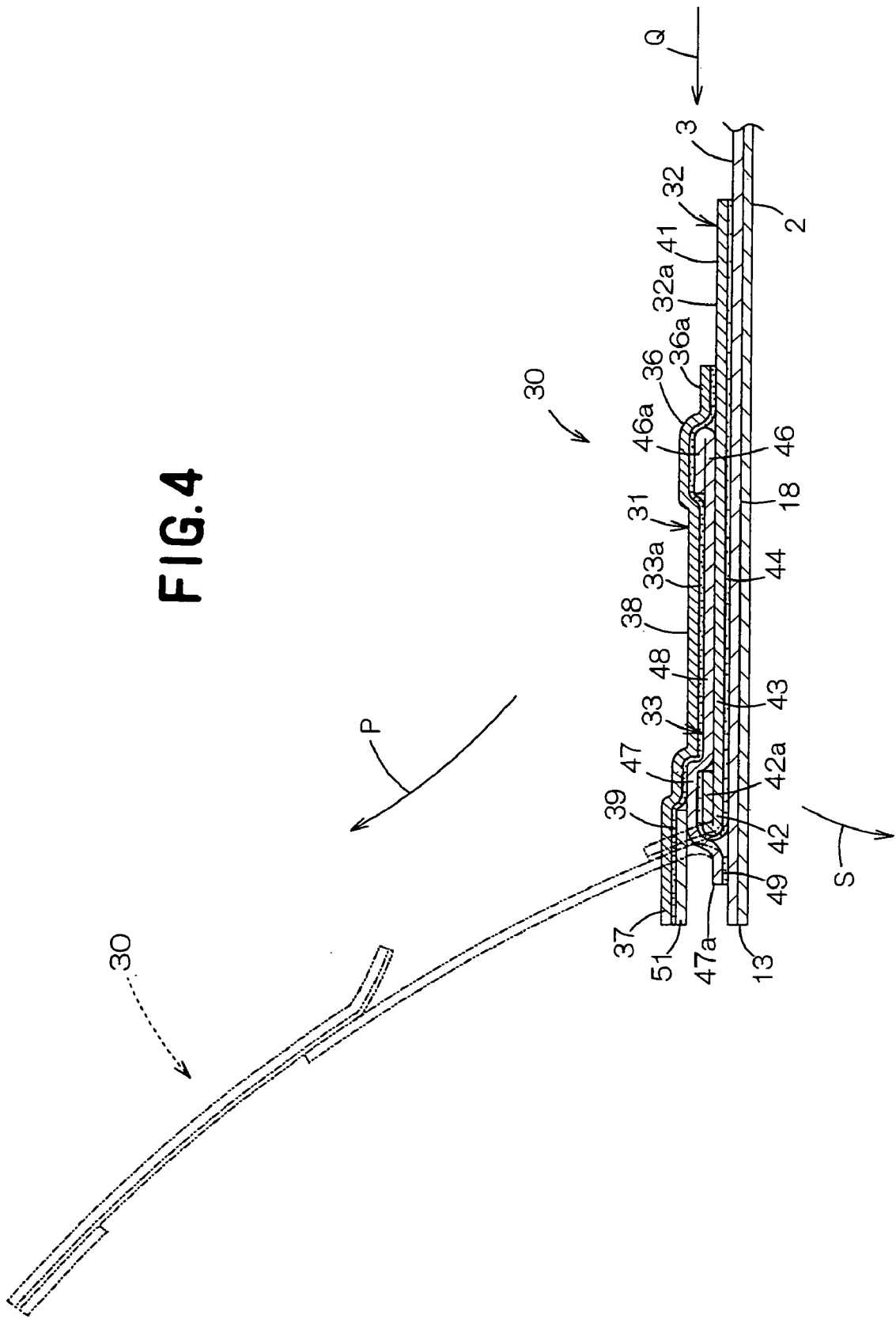
FIG. 4 is a cross-sectional view taken along a line IV-IV in FIG. 1.

FIG. 4 is a cross-sectional view taken along a line IV-IV in FIG. 1. Each of the tape fasteners 30 shown in FIG. 4 has a top tape strip 31, a bottom tape strip 32 and an intermediate tape strip 33 interposed between the top tape strip 31 and the bottom tape strip 32. The top tape strip 31, in turn, has an inner end zone 36, an outer end zone 37 and an intermediate zone 38. The inner surface of these zones 36-38 opposite to the backsheet 3 is coated with a first adhesive 39 which is pressure-sensitive. The bottom tape strip 32 also has an inner end zone 41, an outer end zone 42 and an intermediate zone 43. The inner surface of these zones 41-43 opposed to the backsheet 3 is coated with a second adhesive 44 which is pressure-sensitive. It should be noted that a portion 42a of the outer end zone 42 is folded upwardly as seen in FIG. 4. The intermediate tape strip 33 also has an inner end zone 46, an outer end zone 47 and an intermediate zone 48. An end 47a of the outer end zone 47 opposed to the backsheet 3 is coated on its inner surface with a third adhesive 49 which is pressure-sensitive. A portion 46a of the inner end zone 46 is folded upwardly as seen in FIG. 4.

In the tape fastener 30 arranged as has been described above, the top tape strip 31 has its inner end zone 36 secured to connect to the folded portion 46a of the intermediate tape strip 33 so as not to be peeled off and a portion 36a of the inner end zone 36 extending beyond the intermediate tape strip 33. The portion 36a is releasably attached to an outer surface 32a of the bottom tape strip 32 so as to be peeled off easily. In the outer end zone 37 of the top tape strip 31, the first adhesive 39 is covered with a film strip 51. The intermediate zone 38 of the top tape strip 31 is releasably attached to an outer surface 33a of the intermediate tape strip 33 so as to be peeled off easily.

Almost all over the bottom tape strip 32 is secured to the outer surface (i.e., the upper surface as viewed in FIG. 4) of the backsheet 3 by means of the second adhesive 44 except for the folded portion 42a of the outer end zone 42 so as not to be peeled off. Specifically, the folded portion 42a is secured to connect to the inner surface of the outer end zone 47 of the intermediate tape strip 33 so as not to be peeled off.

The intermediate zone 48 of the intermediate tape strip 33 is not adhered to the outer surface 32a of the bottom tape strip 32 except for the portion 46a folded and adhered to the top tape strip 31 and the outer end zone 47 adhered to the portion 42a of the bottom tape strip 32. Therefore the intermediate tape strip 33 can be peeled off easily from the outer surface 32a. The second adhesive 44 and the third adhesive 49 may be replaced by an adhesive which is curable after coating.

This tape assembly comprising the top tape strip 31, the intermediate tape strip 33 and the bottom tape strip 32 retains a posture folded in a Z-shape prior to actual use of the diaper. With the outer end zone 37 of the top tape strip 31 held together with the film strip 51, the tape fastener 30 is pulled upward obliquely with respect to the backsheet 3 in a direction indicated by an arrow P extending from the bottom tape strip 32 secured to the backsheet 3 toward the deformable outer end zone 37. In consequence, the zones and/or the portions releasably attached one to another are released one from another and the tape fastener 30 is rectilinearly unfolded as indicated by imaginary lines. If the first adhesive 39 has affinity to the bottom tape strip 32 and the intermediate tape strip 33, surfaces of these tape strips 32, 33 may be previously coated with a suitable release agent such as a silicone oil to be peeled off from these tape strips 32, 33.

Figure 5:
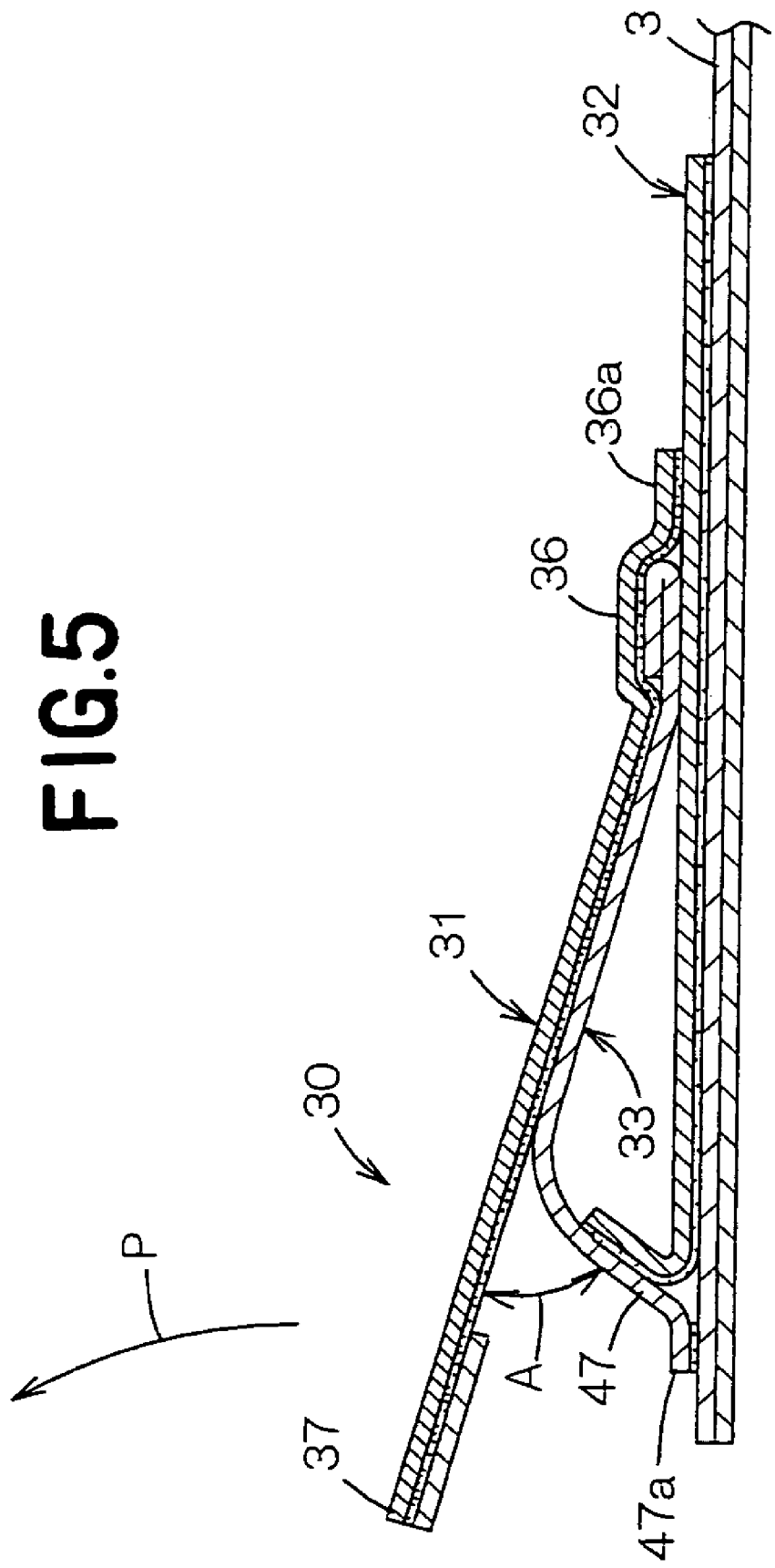
FIG. 5 is a cross-sectional view illustrating the process in which the tape fasteners are unfolded.
Figure 6:
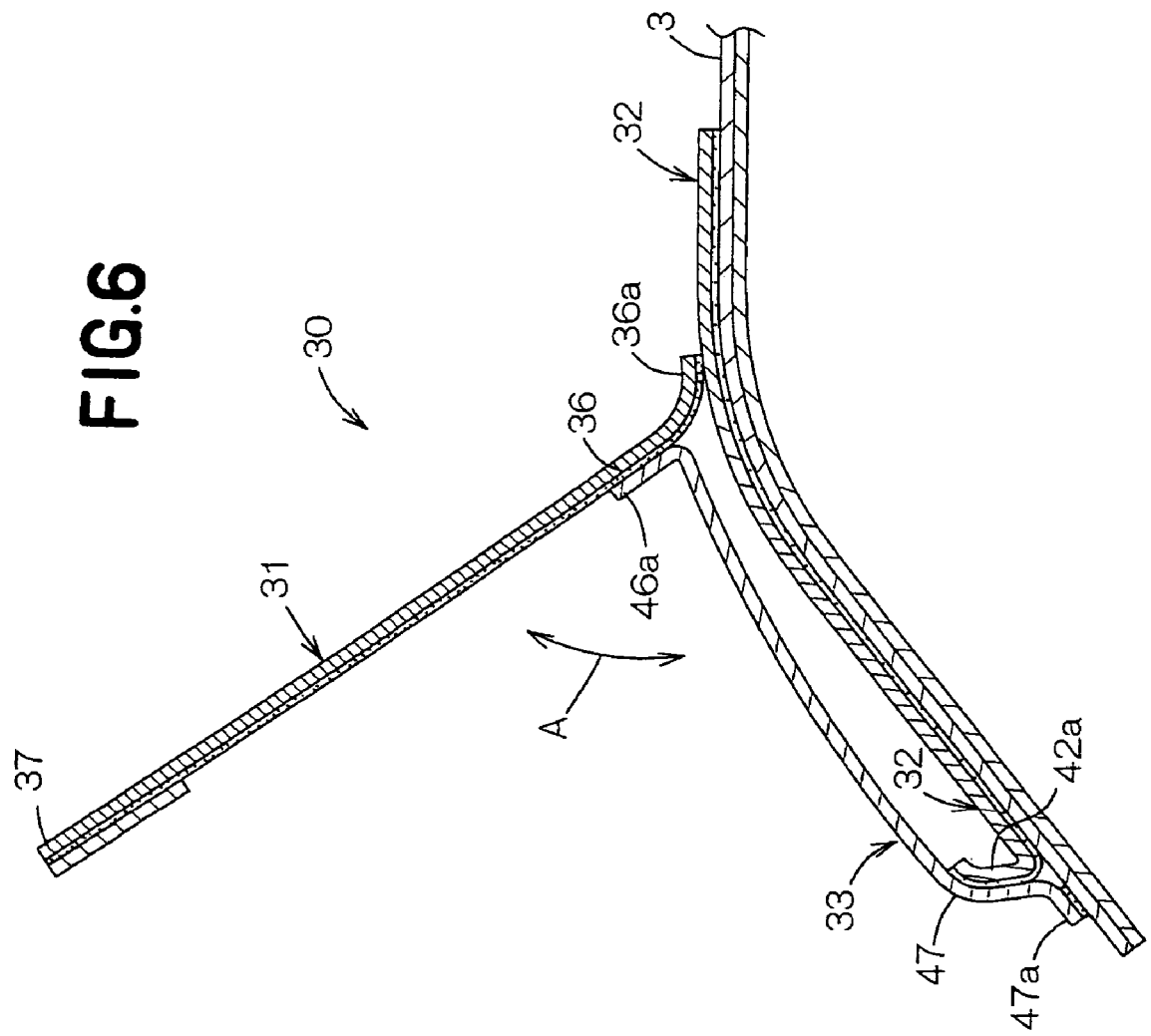
FIG. 6 is a cross-sectional view similar to FIG. 5.

FIGS. 5 and 6 are views similar to FIG. 4, illustrating a process in which the tape fasteners 30 are unfolded. Pulling the outer end zone 37 of the top tape strip 31 upwardly in the direction of the arrow P as shown in FIG. 5 causes the top tape strip 31 to be straightened left- and upwardly between its outer end zone 37 and inner end zone 36 as shown by FIG. 6. Following this movement of the outer end zone 37, a portion of the outer end zone 47 of the intermediate tape strip 33 lying inside the end 47a (i.e., portion on the right side of the end 47a as viewed in FIGS. 5 and 6) secured to the backsheet 3 is pulled upwardly so as to be spaced from the bottom tape strip 32 secured to the backsheet 3. Consequently, an angle A included between the top tape strip 31 and the intermediate tape strip 33 is progressively enlarged. A peel force is exerted between these top tape strip 31 and intermediate tape strip 33 and facilitates these two tape strips 31, 33 to be peeled off from each other. When the top tape strip 31 is further pulled, particularly when the top tape strip 31 is pulled obliquely upwardly so as to enlarge the angle A, a peel force is exerted on the portion 36a of the top tape strip 31 attached to the bottom tape strip 32 and thereby facilitates the portion 36a to be peeled off from the bottom tape strip 32. It should be noted, however, that the inner end zone 36 of the top tape strip 31 is secured to the portion 46a of the intermediate tape strip 33, the outer end zone 47 of the intermediate tape strip 33 is secured to the portion 42a of the bottom tape strip 32 and the bottom tape strip 32 is secured to the backsheet 3. In this way, the tape fastener 30 is rectilinearly unfolded as indicated by the imaginary lines in FIG. 4 as the outer end zone 37 of the top tape strip 31 is pulled.

The tape fastener 30 can be unfolded merely by pulling the outer end zone 37 of the top tape strip 31 upwardly in the direction of the arrow P and this feature facilitates the tape fastener 30 to be handled. Even if a force is exerted on the tape fastener 30 in a direction indicated by an arrow Q (See FIG. 4), it is unlikely that the top tape strip 31 and the intermediate tape strip 33 might be easily peeled off from the bottom tape strip 32 because the portion 36a of the top tape strip 31 is adhered to the bottom tape strip 32 as shown. In other words, the tape fastener 30 is free from an inconvenience that the respective tapes might be unintentionally peeled off before the diaper is put on baby's body and an operation of putting the diaper on the baby's body might take much time and effort as the conventional tape fastener folded in a Z-shape has often been the case. The tape fastener 30 according to the present embodiment of this invention is so arranged that the top tape strip 31 is peeled off from the intermediate tape strip 33 successively from its outer end zone 37 toward its inner end zone 36 and finally the portion 36a of the inner end zone 36 is peeled off from the bottom tape strip 32. With such an arrangement, even if a series of peeling the top tape strip 31 off from the other tape strips is stopped in mid way, it will be easy to set back the tape fastener 30 to its initial Z-posture as shown in FIG. 4 so far as the portion 36a has not been peeled off from the bottom tape strip 32.

In order to ensure that the tape fastener 30 can be more easily unfolded in the direction of the arrow P, a flexural stiffness of a laminated sheet portion underlying the tape fastener 30 and comprising the bottom tape strip 32, to which the inner end zone 36 of the top tape strip 31 is releasably attached, the backsheet 3 and the topsheet 2, which are overlaid and joined together should be preferably in a range of $(0.03-0.7) \times 10^{-4} N \cdot m^2/m$ in a direction S which intersects with the direction in which the tape fastener 30 is unfolded. The tape fastener 30 can be easily deformed as shown in FIGS. 5 and 6 so far as the side flap 18 exhibits a flexural stiffness in the range. It should be noted, however, that the flexural stiffness of the side flap 18 exceeding $0.7 \times 10^{-4} N \cdot m^2/m$ would disadvantageously deteriorate feeling to wear the diaper 1.

Figure 7:
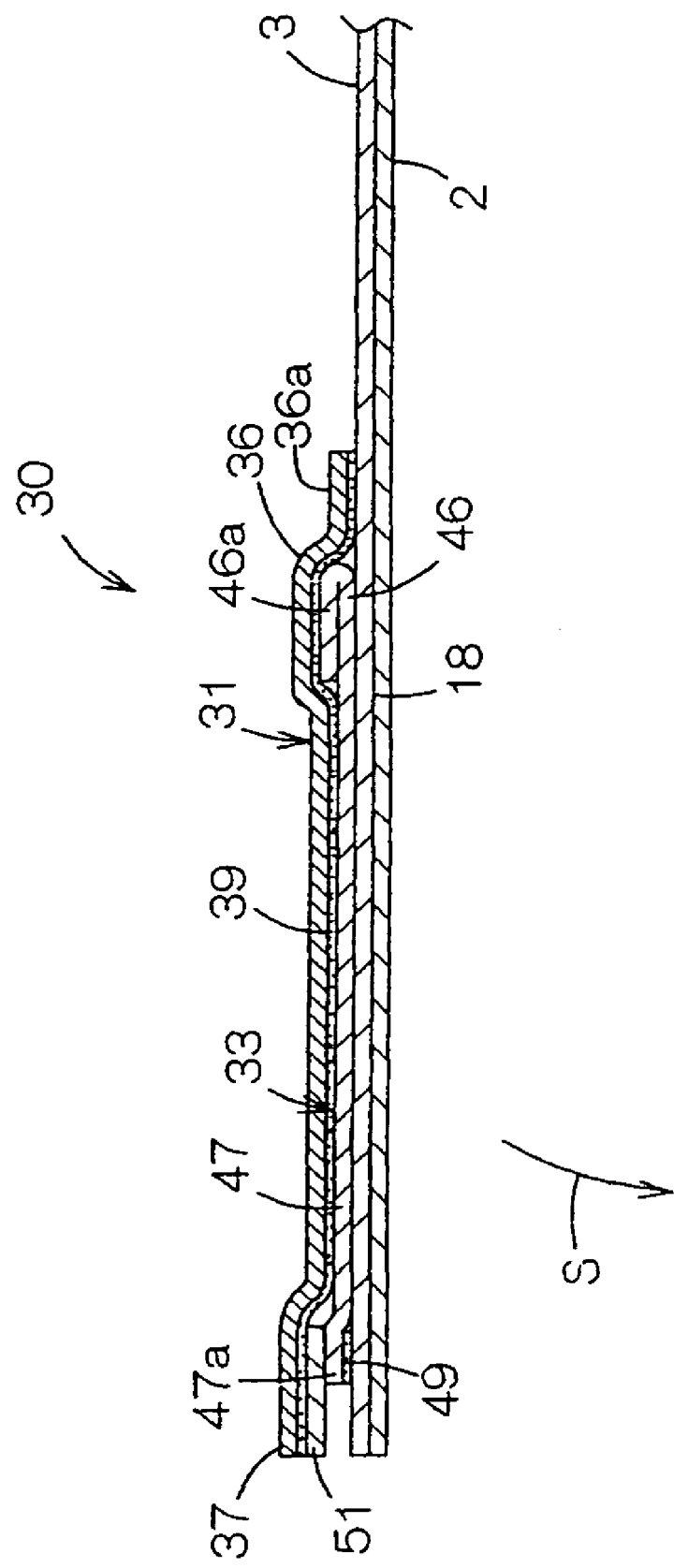
FIG. 7 is a view similar to FIG. 4 showing a preferred embodiment of this invention.

FIG. 7 is a view similar to FIG. 4, showing one preferred embodiment of this invention. In the case of this alternative embodiment, the tape fastener 30 comprises the top tape strip 31 and the intermediate tape strip 33 shown in FIG. 4 and does not include the bottom tape strip 32 shown in FIG. 4. Of the intermediate tape strip 33, the end 47a of the outer end zone 47 is secured to the backsheet 3 by means of the third adhesive 49 and the portion lying inside the end 47a is not adhesively attached to the backsheet 3. The folded portion 46a of the inner end zone 46 is adhered to the inner surface of the inner end zone 36 of the top tape strip 31. The inner end zone 36 of the top tape strip 31 also includes the edge portion 36a extending inwardly of the diaper 1 beyond the folded edge portion 46a of the intermediate tape strip 33. The portion 36a is releasably attached to the backsheet 3 by means of the first adhesive 39. In the top tape strip 31, the first adhesive 39 applied on the outer end zone 37 is covered with the film strip 51 but exposed on the portion lying aside from the film strip 51 toward the inner end zone 36. The exposed portion of the first adhesive 39 attaches the top tape 31 releasably to the inner side of the intermediate tape strip 33 in the vicinity of the inner end zone 46 beyond the end 47a. The tape fastener 30 according to this embodiment also can be unfolded as easily as the embodiment shown in FIG. 4 and its arrangement is simpler than that of the embodiment shown in FIG. 4. However, with this embodiment of the tape fastener 30, the force required to pull the top tape strip 31 is directly exerted on the backsheet 3 at the portion 36a of the top tape strip 31 and at the end 47a of the intermediate tape strip 33. Taking account of this, this tape fastener 30 is preferably used with the backsheet 3 having a high strength.

In the embodiment shown in FIG. 7 also, the flexural stiffness of the laminated sheet portion underlying the tape fastener 30 and comprising the backsheet 3 and the topsheet 2 overlaid and joined each other should be preferably in a range of $(0.03-0.7) \times 10^{-4} N \cdot m^2/m$. The laminated sheet portion includes a region in which the inner end zone 36 of the top tape strip 31 is releasably attached to the backsheet 3. When the topsheet 2 is not adhesively attached to the backsheet 3 immediately under the tape fastener 30, a flexural stiffness of the backsheet 3 alone is preferably in a range of $(0.03-0.7) \times 10^{-4} N \cdot m^2/m$.

Figure 8:
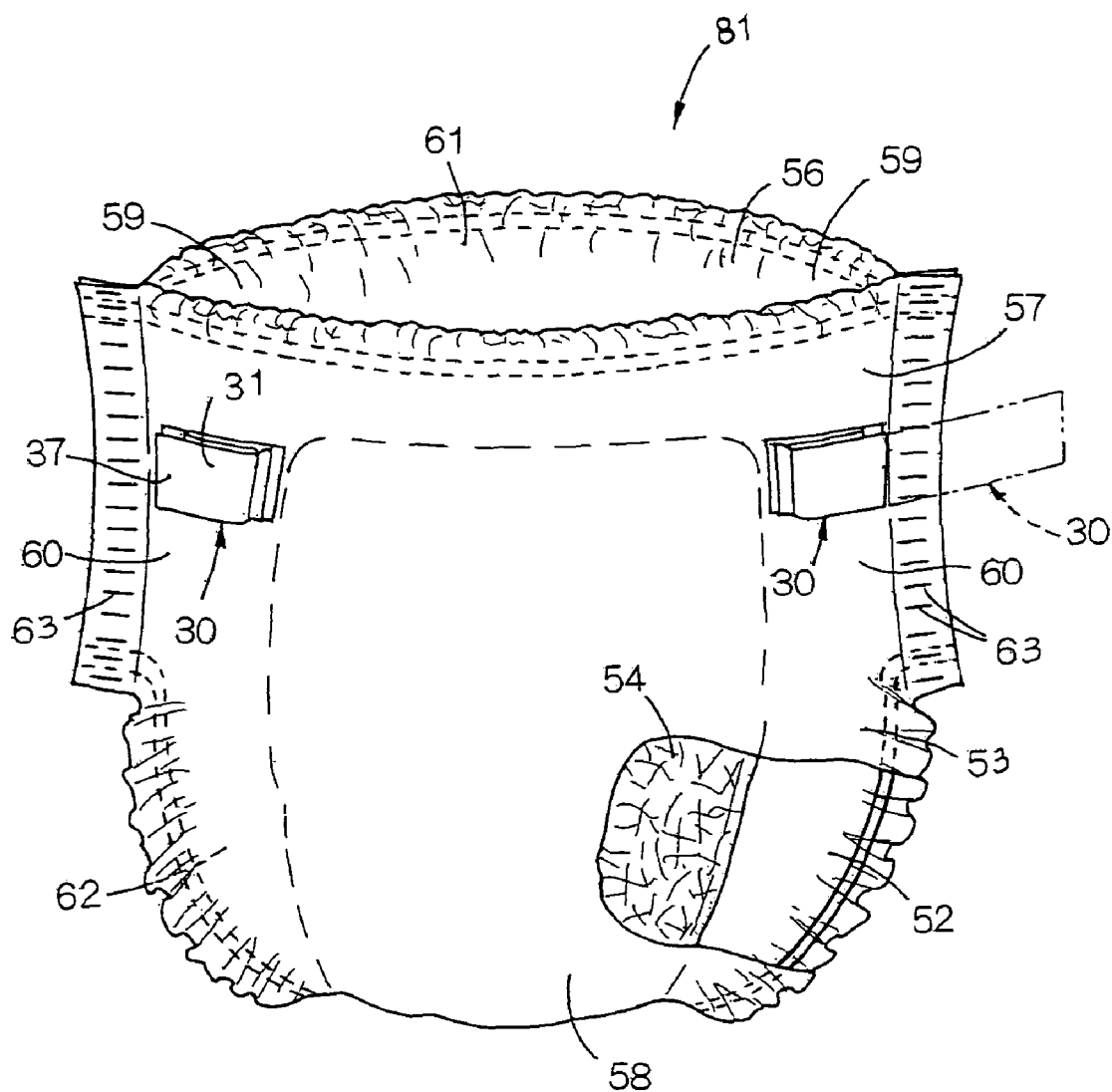
FIG. 8 is a perspective view showing another preferred embodiment of this invention.
Figure 9:
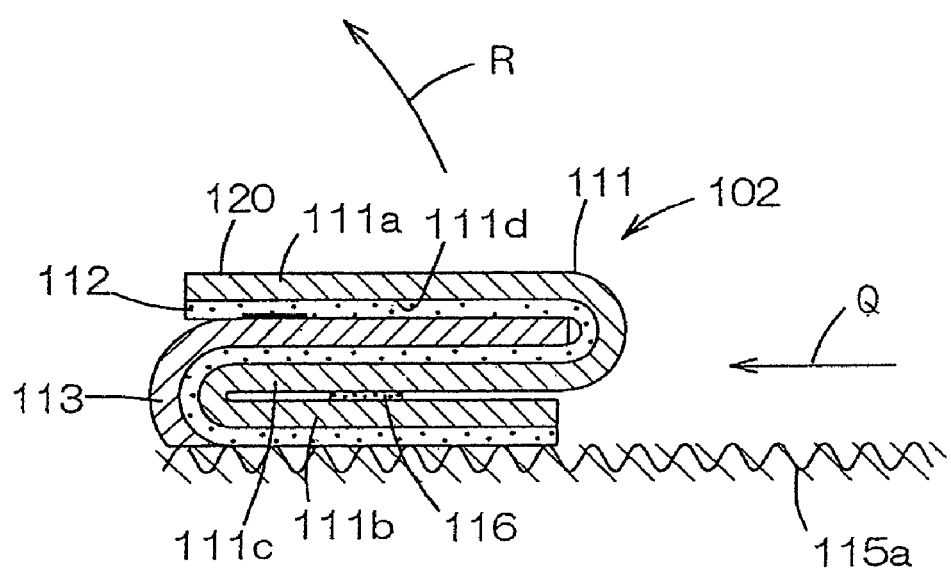
FIG. 9 is a side view showing the tape fasteners of prior art.

FIG. 8 is a partially cutaway perspective view showing a pants-type disposable diaper 81 as another preferred embodiment of this invention. This diaper 81 comprises a topsheet 52, a backsheet 53 and a core 54 disposed between these two sheets 52, 53. The diaper 81 is composed of a front waist region 56, a rear waist region 57 and a crotch region 58. The top- and backsheets 52, 53 extend outward beyond a peripheral edge of the core 54 to form transversely opposite side edge portions 59, 60 of the front and rear waist regions 56, 57, respectively. These side edge portions 59, 60 are joined together at a plurality of regions so that the front and rear waist regions 56, 57 cooperate with the crotch region 58 to form a waist-hole 61 and a pair of leg-holes 62. Tape fasteners 30 similar to those shown in FIG. 4 are disposed to the diaper 81 on the side edge portions 60 or 59 of the rear waist region 57 or the front waist region 56, respectively, so as to extend in a waist-surrounding direction. In the case of the illustrated embodiment, these tape fasteners 30 are disposed to the rear waist region 57. The tape fastener 30 is unfolded rectilinearly as indicated by imaginary lines as the outer end zone 37 of the top tape strip 31 is held and pulled. The tape fasteners 30 disposed to the diaper 81 serve as fastening means not only when the diaper 81 is put on the wearer's body but also when the used diaper 81 is rolled up for disposal.

While the invention has been described with respect to the disposable diaper 1, 81, this invention is applicable also to the other disposable wearing article such as disposable training pants or disposable medical gown. Film of plastic such as polyester, polypropylene, polyethylene or urethane may be used as a stock material for the top tape strip 31, bottom tape strip 32 and the intermediate tape strip 33. The first, second and third adhesives 39, 44, 49 preferably have a high affinity to the film to be coated with these adhesives.

With the disposable wearing article provided with the tape fasteners, the fastener tape comprises the top tape strip and the intermediate tape strip folded on each other so that the outer end zone of the top tape strip may be held and pulled upwardly to stretch the top tape strip and simultaneously to enlarge the angle included between the top tape strip and the intermediate tape strip underlying the top tape strip. In this way, the top tape strip can be easily peeled off from the intermediate tape strip. The inner end zone of the top tape strip may be releasably attached to the surface of the wearing article facing the undergarment to prevent the folded tape fasteners from being unintentionally unfolded.

What is claimed is:

1. A disposable wearing article having a first surface adapted to face a wearer's body and a second surface adapted to face away from the wearer's body, said article comprising an adhesive tape fastener which is disposed on said second surface in a folded state and which is unfoldable from the folded state to an unfolded state, said tape fastener having a free end zone and a fixed end zone opposed to each other in a longitudinal direction of said tape fastener in the unfolded state, said fixed end zone being directly secured to said second surface, said tape fastener being unfoldable from the folded state to the unfolded state by holding and pulling said free end zone in a unfolding direction away from both said fixed end zone and said second surface, said tape fastener having an inner surface which faces said second surface in the unfolded state and is partially coated with an adhesive, said tape fastener further comprising:

a first monolithic tape strip which has said free end zone, a first end zone opposed to said free end zone in said longitudinal direction, and a first middle zone located between said free end zone and said first end zone; and a second monolithic tape strip which underlies said first tape strip in the folded state so as to face said second surface and has said fixed end zone, a second end zone opposed to said fixed end zone in said longitudinal direction, and a second middle zone located between said fixed end zone and said second end zone;

wherein said first end zone of said first tape strip is adhesively connected to said second end zone of said second tape strip;

the first middle zone of said first tape strip is coated on said inner surface with said adhesive so as to be releasably attached by said adhesive to the second middle zone of said second tape strip underlying said first tape strip in the folded state;

said first end zone includes an extension extending away from said free end zone and beyond said second end zone of said second tape strip and being directly releasably attached to said second surface in the folded state; and in the folded state, the second middle zone and the second end zone of said second tape strip are directly contactable with and free of direct attachment to said second surface so as to be liftable upwardly off said second surface when said tape fastener is unfolded; and wherein said article has a front waist region, a rear waist region, a crotch region extending between said waist regions, and an absorbent core in said crotch region;

said article comprises two said tape fasteners;

each of said waist regions has an end portion and two transversely opposite side edge portions;

the end portions of said waist regions are adapted to define together a waist hole;

said free end zone of said first tape strip of each of said tape fasteners is located on said second surface in one of said side edge portions of one of said front and rear waist regions so that, in the folded state, a longitudinal direction of said first tape strip is parallel to a waist-surrounding direction of said waist-hole and the first end zone is inwardly spaced from said free end zone; and said fixed end zone of said second tape strip of each of said tape fasteners is adhesively and directly attached to said second surface in the one of said side edge portions of said one of said front and rear waist regions so that entire said second tape strip is interposed between said first tape strip and said second surface when said respective tape fastener is in the folded state in which the free and fixed end zones are closer to a longitudinal edge of the respective side edge portion than the first and second end zones.

2. The disposable wearing article according to claim 1, wherein said disposable wearing article is a pants-type disposable diaper, said front and rear waist regions are permanently connected together at a plurality of bonding sites along the side edge portions so as to form the waist-hole and a pair of leg-holes, and a longitudinal direction of said second tape strip of each said tape fastener is parallel to the waist-surrounding direction of the waist-hole.

3. The disposable wearing article according to claim 2, wherein said disposable diaper has flaps formed by a sheet material extending outwardly beyond a peripheral edge of said core; and said fixed end zone of the second tape strip of each of said tape fasteners is adhesively attached to said second surface in one of said flaps.

4. The article according to claim 2, wherein said free end zone of said first tape strip of each of said tape fasteners is adjacent to the bonding sites where the side edge portions of said front and rear waist regions are permanently connected.

5. The disposable wearing article according to claim 1, wherein said article comprises a topsheet, a backsheet and the absorbent core disposed between the topsheet and backsheet; and in the folded state, the extension of said first end zone of said first tape strip is directly releasably attached to the second surface at a laminated sheet portion which underlies each said tape fastener and has a flexural stiffness of from 0.03×10$^{-4}$N·m$^2$/m to 0.07×10$^{-4}$N·m$^2$/m, said laminated sheet portion comprising the backsheet and the topsheet.

6. The disposable wearing article according to claim 5, wherein said flexural stiffness is measured in a direction perpendicular to the unfolding direction of the tape fastener.

7. The disposable wearing article according to claim 1, wherein, in the folded state of each said tape fastener, an entirety of said first tape strip, except said extension, is free of direct attachment to said second surface.

8. The disposable wearing article according to claim 1, wherein, in each said tape fastener, an entire length of the first middle zone located between said free end zone and said first end zone of said first tape strip is coated with said adhesive.

9. The article according to claim 1, wherein
an end edge of said free end zone of each said tape fastener is even with a side edge of the one of said side edge portions of said one of said front and rear waist regions.

10. The article according to claim 1, wherein each said tape fastener consists of:
said first and second tape strips;
said adhesive which connects the first and second end zones, releasably attaches the first and second middle zones together, and releasably attaches the extension to said second surface; and
a film which covers the adhesive coated on the free end zone and prevents the free end zone from being directly attached to any of said second tape strip and said second surface.

11. A disposable wearing article having a first surface adapted to face a wearer's body and a second surface adapted to face away from the wearer's body, said article comprising an adhesive tape fastener which is disposed on said second surface in a folded state and which is unfoldable from the folded state to an unfolded state,
said tape fastener having a free end zone and a fixed end zone opposed to each other in a longitudinal direction of said tape fastener in the unfolded state,
said fixed end zone being secured to said second surface,
said tape fastener being unfoldable from the folded state to the unfolded state by holding and pulling said free end zone in a unfolding direction away from both said fixed end zone and said second surface,
said tape fastener having an inner surface which faces said second surface in the unfolded state and is partially coated with an adhesive,
said tape fastener further comprising:
a first monolithic tape strip which has said free end zone, a first end zone opposed to said free end zone in said longitudinal direction, and a first middle zone located between said free end zone and said first end zone;
a second monolithic tape strip which underlies said first tape strip in the folded state so as to face said second surface and has said fixed end zone, a second end zone opposed to said fixed end zone in said longitudinal direction, and a second middle zone located between said fixed end zone and said second end zone; and
a third monolithic tape strip which is interposed between said second tape strip and said second surface in the folded state, and which is directly secured over substantially a full length thereof to said second surface;
wherein
said fixed end zone is indirectly attached to said second surface via said third tape strip;
said first, second and third tape strips together define a Z-shape when the tape fastener is in the folded state;
said first end zone of said first tape strip is adhesively connected to said second end zone of said second tape strip;
the first middle zone of said first tape strip is coated on said inner surface with said adhesive so as to be releasably attached by said adhesive to the second middle zone of said second tape strip underlying said first tape strip in the folded state;
said first end zone includes an extension extending away from said free end zone and beyond said second end zone of said second tape strip and being directly releasably attached to said third tape strip in the folded state; and
in the folded state, the second middle zone and the second end zone of said second tape strip are free of direct attachment to said third tape strip so as to be liftable upwardly off said third tape strip when said tape fastener is unfolded; and
wherein
said article has a front waist region, a rear waist region, a crotch region extending between said waist regions, and an absorbent core in said crotch region;
said article comprises two said tape fasteners;
each of said waist regions has an end portion and two transversely opposite side edge portions;
the end portions of said waist regions are adapted to define together a waist hole;
said free end zone of said first tape strip of each of said tape fasteners is located on said second surface in one of said side edge portions of one of said front and rear waist regions so that, in the folded state, a longitudinal direction of said first tape strip is parallel to a waist-surrounding direction of said waist-hole and the first end zone is inwardly spaced from said free end zone;
said fixed end zone of said second tape strip of each of said tape fasteners is adhesively attached to said second surface in the one of said side edge portions of said one of said front and rear waist regions so that entire said second tape strip is interposed between said first tape strip and said second surface when said respective tape fastener is in the folded state in which the free and fixed end zones are closer to a longitudinal edge of the respective side edge portion than the first and second end zones; and
said fixed end zone of each said tape fastener is secured to the second surface both directly and indirectly, said fixed end zone having a first portion directly secured to the second surface and a second portion indirectly secured to the second surface via the third tape strip, wherein said first portion is closer to the longitudinal edge of the respective side edge portion than the second portion, and is spaced from the second portion by a third portion free of direct attachment to both said second surface and said third tape strip.

12. The disposable wearing article according to claim 11, wherein, in the folded state of each said tape fastener, an entirety of said first tape strip, except said extension, is free of direct attachment to said third tape strip.

13. The disposable wearing article according to claim 11, wherein, in each said tape fastener, an entire length of the first middle zone located between said free end zone and said first end zone of said first tape strip is coated with said adhesive.

14. The disposable wearing article according to claim 11, wherein
said article comprises a topsheet, a backsheet and the absorbent core disposed between the topsheet and backsheet;

in the folded state of each said tape fastener, the extension of said first end zone of said first tape strip is directly releasably attached to said third tape strip at a laminated sheet portion that has a flexural stiffness of from $0.03 \times 10^{-4} N \cdot m^2/m$ to $0.07 \times 10^{-4} N \cdot m^2/m$;

said flexural stiffness is measured in a direction perpendicular to the unfolding direction of the tape fastener; and said portion having said flexural stiffness includes said backsheet, topsheet and third tape strip.

15. The article according to claim 11, wherein
an end edge of said free end zone of each said tape fastener is even with a side of the one of said side edge portions of said one of said front and rear waist regions.

16. A disposable wearing article, comprising:
a main body having a front waist region, a rear waist region and a crotch region extending in a longitudinal direction of said main body between said front and rear waist regions; and
a tape fastener attached to said main body;
wherein
said tape fastener comprises a first monolithic tape strip and a second monolithic tape strip, each of said tape strips having opposite first and second end zones, the second end zones of said tape strips being adhesively connected to each other, the first end zone of said second tape strip being permanently directly attached to one of opposite surfaces of said main body, said surface being adapted to face away from a wearer's body, in use;
said tape fastener is in a folded state in which
entire said second tape strip is sandwiched between said first tape strip and said surface of said main body,
the second end zone of said first tape strip has an extension that is directly releasably attached to said surface of said main body, and
said second tape strip is directly releasably attached to said first tape strip in a middle zone located between said first and second end zones of said second tape strip;
said tape fastener is unfoldable from said folded state to a unfolded state in which the second end zones of said tape strips are free of direct attachment to said surface of said main body while remaining connected to each other; and
in the folded state, an entirety of said second tape strip, except the first end zone thereof, is free of direct attachment to said surface of said main body so as to be liftable upwardly off said surface of said main body when said tape fastener is unfolded; and
in the folded state, the first end zone of said first tape strip, which is a free end zone, has an outermost end edge even with a longitudinal side edge of one of the waist regions, and the first end zone of said second tape strip is closer to said longitudinal side edge than the second end zone of said second tape strip.

17. The disposable wearing article according to claim 16, wherein, in the folded state, an entirety of said first tape strip, except said extension, is free of direct attachment to said surface of said main body.

18. The disposable wearing article according to claim 16, wherein an entire length between and inclusive of the first and second end zones of said first tape strip is coated with an adhesive layer which, in the folded state, releasably attaches both (a) said extension to said surface of said main body, and (b) said first tape strip to said second tape strip in the middle zone of said second tape strip.

19. The disposable wearing article according to claim 18, wherein said adhesive layer extends continuously over said entire length.

20. The article of claim 18, wherein
said main body comprises a topsheet, a backsheet and an absorbent core disposed between the topsheet and backsheet;
a third tape strip is permanently attached to said backsheet by a further adhesive layer and defines a portion of the surface of said main body to which the extension of said first end zone of said first tape strip is directly releasably attached; and
in the folded state of said tape fastener,
a portion of said third tape strip is folded up onto itself to define a lower fold and an upper fold overlying said lower fold,
said further adhesive layer has a region located between and permanently attaching the lower fold of said third tape strip to said backsheet,
said further adhesive layer has another region located between and permanently attaching the first end zone of said second tape strip and the upper fold of said third tape strip, and
said first end zone of said second tape strip has a further extension which extends away from said second end zone of said second tape strip and beyond said upper fold of said third tape strip and which is directly attached to said backsheet.

21. The disposable wearing article according to claim 16, wherein
a length between and inclusive of the first and second end zones of said first tape strip is coated with an adhesive layer which, in the folded state, releasably attaches both (a) said extension to said surface of said main body, and (b) said first tape strip to said second tape strip in the middle zone of said second tape strip;
said tape fastener further comprises a film covering the adhesive layer coated on the first end zone of said first tape strip and preventing the first end zone of said first tape strip from being directly attached to any of said second tape strip and said surface of said main body;
said film comprises an inner portion and an outer portion further from the second end zone of said first tape strip than the inner portion;
in the folded state, the inner portion of said film is located above, directly physically contacts with and rests on the first end zone of said second tape strip, whereas the outer portion of said film projects beyond a boundary of said first end zone of said second tape strip.

22. The article of claim 18, wherein, in the folded state of said tape fastener, the second end zone of said second tape strip is folded up onto itself to define a lower fold and an upper fold overlying said lower fold;
said adhesive layer further permanently attaching the second end zone of said first tape strip and the upper fold.

23. The article of claim 22, further comprising a release agent coated on an upper surface of said second tape strip and allowing the adhesive layer to be releasably attached to said second tape strip.

* * * * *